US008198319B2

(12) United States Patent
Ahrens et al.

(10) Patent No.: US 8,198,319 B2
(45) Date of Patent: Jun. 12, 2012

(54) COMPOSITION AND METHOD FOR TREATING DIABETES AND METABOLIC DISORDERS

(76) Inventors: Milton Joseph Ahrens, Lake Alfred, FL (US); Daryl Lee Thompson, Winter Haven, FL (US)

( * ) Notice: Subject to any disclaimer, the term of this patent is extended or adjusted under 35 U.S.C. 154(b) by 0 days.

(21) Appl. No.: 13/014,798

(22) Filed: Jan. 27, 2011

(65) Prior Publication Data

US 2011/0118345 A1 May 19, 2011

Related U.S. Application Data

(62) Division of application No. 12/045,852, filed on Mar. 11, 2008, now Pat. No. 7,943,164.

(60) Provisional application No. 60/895,486, filed on Mar. 19, 2007.

(51) Int. Cl.
*A61K 31/352* (2006.01)
(52) U.S. Cl. ........................................... 514/456
(58) Field of Classification Search ................ None
See application file for complete search history.

(56) References Cited

U.S. PATENT DOCUMENTS

| 5,565,435 | A  | 10/1996 | Yoneyama et al. |
| 6,096,364 | A  | 8/2000  | Bok et al. |
| 7,229,651 | B2 | 6/2007  | Perkes |
| 7,270,837 | B2 | 9/2007  | Vorsa et al. |
| 2002/0054924 | A1 | 5/2002 | Leahy et al. |
| 2003/0108627 | A1 | 6/2003 | Seizer et al. |
| 2003/0133945 | A1 | 7/2003 | Farley |
| 2005/0181076 | A1 | 8/2005 | Ziegler |
| 2006/0035971 | A1 | 2/2006 | Arai et al. |
| 2006/0111435 | A1 | 5/2006 | Sinclair et al. |
| 2006/0188590 | A1 | 8/2006 | Ono |
| 2007/0092454 | A1 | 4/2007 | Cameron et al. |
| 2008/0234364 | A1 | 9/2008 | Ahrens et al. |

FOREIGN PATENT DOCUMENTS

| EP | 0969743 | 9/2004 |
| WO | 2006/024545 | 3/2006 |
| WO | 2006/074278 | 7/2006 |

OTHER PUBLICATIONS

Hemmerle H. et al; Chlorogenic Acid and Synthetic Chlorogenic Acid Derivatives: Novel Inhibitors of Hepatic Glucose-6-phosphate Translocase, Journal of Medicinal Chemistry, American Chemical Society, vol. 40, No. 2, Jan. 17, 1997, pp. 137-145.
Knekt P. et al; Flavonoid intake and risk of chronic diseases, American Journal of Clinical Nutrition, vol. 76, No. 3, Sep. 1, 2002, pp. 560-568.
Strobel P. et al; Myricetin, quercetin and catechin-gallate inhibit glucose uptake in isolated rat adipocytes, Biochemical Journal, vol. 386, Mar. 2005, pp. 471-478.
Wilson T. et al; Human Glycemic Response and Phenolic Content of Unsweetened Cranberry Juice, Journal of Medicinal Food, vol. 11, No. 1, Mar. 1, 2008, pp. 46-54.
Chen H. et al; Separation and determination of flavonoids and other phenolic compounds in cranberry juice by high-performance liquid chromatography, Journal of Chromatography, vol. 913, No. 1-2, Apr. 13, 2001, pp. 387-395.
International Search Report and the Written Opinion of the corresponding International Application No. PCT/US2008/056474 mailed Aug. 5, 2008.
Dharmananda, Oriental Perspectives on Cancer and It's Treatment, May 1997, pp. 1-8.

*Primary Examiner* — Tracy Vivlemore
*Assistant Examiner* — Jennifer Berrios
(74) *Attorney, Agent, or Firm* — Renner, Otto, Boisselle & Sklar, LLP

(57) ABSTRACT

A composition and method for treating diabetes and metabolic disorders, and for achieving weight loss in a subject comprising a combination of naturally occurring compounds is provided.

9 Claims, No Drawings

COMPOSITION AND METHOD FOR TREATING DIABETES AND METABOLIC DISORDERS

This application is a divisional of U.S. Patent Application No. 12/045,852, filed on Mar. 11, 2008 now U.S. Pat. No. 7,943,164 and claims the benefit of U.S. Provisional Application No. 60/895,486, filed on Mar. 19, 2007, the entire contents of which are hereby incorporated by reference.

BACKGROUND

According to the American Heart Association, over 60% of men and nearly 50% of women are overweight. Furthermore, approximately 13% and 18% of men and women, relatively, are obese. Being sedentary and overweight can lead to metabolic syndrome, which is characterized by a group of metabolic risk factors in one person. They include: (a) central obesity, indicated by excessive fat tissue in and around the abdomen; (b) atherogenic dyslipidemia (blood fat disorders, mainly high triglycerides and low HDL cholesterol, that foster plaque buildups in artery walls); (c) elevated blood pressure (130/85 mmHg or higher); (d) insulin resistance or glucose intolerance (the body can't properly use insulin or blood sugar); (e) prothrombotic state (e.g., high fibrinogen or plasminogen activator inhibitor [−1] in the blood); and (f) pro-inflammatory state (e.g., elevated high-sensitivity C-reactive protein in the blood).

The underlying causes of this syndrome are overweight/obesity, physical inactivity and genetic factors. People with metabolic syndrome are at increased risk of coronary heart disease, other diseases related to plaque buildup in artery walls (e.g., stroke and peripheral vascular disease) and Type 2 diabetes. According to the American Diabetes Association, 20.6% of adults over the age of 60 have diabetes and 34.8% of all adults have either diabetes or pre-diabetes. Metabolic syndrome has become increasingly common in the United States. It is estimated that about 20-25 percent of U.S. adults are affected. The syndrome is closely associated with a generalized metabolic disorder called insulin resistance, in which the body cannot use insulin efficiently. Metabolic syndrome is also called insulin resistance syndrome, which leads to Type 2 diabetes.

There have been many studies reporting the health benefits provided by bioflavonoids isolated from various plants. The potential role of bioflavonoids in the prevention of cancers and cardiovascular disease and the treatment of inflammatory diseases has been documented. Thousands of naturally occurring bioflavonoids derived from various plants have been classified according to their chemical structure. These classes are flavones, isoflavones, flavan-3-ols and anthocyanidins. Flavones are divided into four groups: (1) flavones, which include, e.g., luteolin, apigenin and tangeritin; (2) flavonols, which include, e.g., quercetin, kaempferol, myricetin, chrysin, rutin, rhoifolin, morin, fisetin, isorhamnetin, pachypodol and rhamnazin; (3) flavanones, which include, e.g., galangin, hesperetin, naringenin, naringin, neohesperidin, hesperidin, narirutin, pruning, eriodictyol, homoeriodictyol; and (4) 3-hydroxyflavanones or 2,3-dihydroflavonols, which include, e.g., dihydroquercetin and dihydrokaempferol. Examples of isoflavones include, e.g., genistein, daidzein and glycitein. Flavan-3-ols include, e.g., catechins, gallocatechin, catechin 3-gallate, gallocatechin 3-gallate, epicatechins, epigallocatechin, epicatechin 3-gallate and epigallocatechin 3-gallate. Anthocyanidins include, e.g., cyanidin, delphinidin, malvidin, perlargonidin, peionidin and petunidin.

Flavonoid availability and activity varies greatly among the natural sources of flavonoids. In order to obtain the healthful benefits of many flavonoids, large doses are required, which is often impractical and too costly.

SUMMARY

In one aspect of the invention, there is provided a composition for treating diabetes and metabolic disorders. The composition is also useful for achieving weight loss and weight control by preventing much of the calories of a carbohydrate-containing food from having an impact. Consumption of the composition with a carbohydrate-containing foodstuff affects the metabolic pathways of carbohydrate metabolism, resulting in less glucose getting into the body and more glucose in the bloodstream getting shunted to the muscles. Consumption of the composition by a subject promotes an increase in the ratio between lean and adipose tissue in the subject.

The present invention provides a composition and a method for treating or preventing diabetes and/or obesity using a combination of naturally occurring compounds. In one embodiment, the method comprises administering to a subject a composition comprising therapeutically effective amounts of quercetin, myricetin and chlorogenic acid. The composition may be administered as a dietary supplement or as an additive to a foodstuff.

The composition is effective in interrupting the metabolic pathways of carbohydrate metabolism. Specifically, the composition is effective in inhibiting glucose absorption in the gut, enhancing glucose absorption by muscle tissue, inhibiting carbohydrate transport, inhibiting glucose/fat storage and inhibiting the manufacture of glucose by the liver (gluconeogenesis).

In one aspect of the invention there is provided a composition and method for lowering the glycemic index of a carbohydrate-containing foodstuff by adding to the foodstuff effective amounts of quercetin, myricetin and chlorogenic acid. In one embodiment the ratio of chlorogenic acid to quercetin to myricetin is about 1:3:3 by weight.

DETAILED DESCRIPTION

As used herein, the following terms and phrases shall have the meaning set forth below.

"Diabetes refers to high blood sugar or ketoacidosis, as well as chronic, general metabolic abnormalities arising from a prolonged high blood sugar status or a decrease in glucose tolerance. "Diabetes" encompasses both the Type 1 and Type 2 (Non Insulin Dependent Diabetes Mellitus or NIDDM) forms of the disease.

"Isolated" refers to the removal or change of a composition or compound from its natural context.

The phrase "naturally occurring" when referring to a compound means a compound that is in a form in which it can be found naturally. A compound is not in a form that is naturally occurring if, for example, the compound has been purified and separated from at least some of the other molecules that are found with the compound in nature. A "naturally occurring compound" refers to a compound that can be found in nature, i.e., a compound that has not been designed by man. A naturally occurring compound may have been made by man or by nature.

"Treating" a condition or disease refers to curing as well as ameliorating at least one symptom of the condition or disease.

The term "therapeutic effect" is art-recognized and refers to a local or systemic effect in animals, particularly mammals, and more particularly humans caused by a pharmacologically active substance. The phrase "therapeutically effective amount" means that amount of such a substance that produces some desired local or systemic effect at a reasonable benefit/risk ratio applicable to any treatment. The therapeutically effective amount of such substance will vary depending upon the subject and disease or condition being treated, the weight and age of the subject, the severity of the disease or condition, the manner of administration and the like, which can readily be determined by one or ordinary skill in the art. For example, certain compositions described herein may be administered in a sufficient amount to produce a desired effect at a reasonable benefit/risk ratio applicable to such treatment.

The glycemic index (GI) is a ranking of carbohydrates on a scale from 0 to 100 based on the extent to which they raise blood sugar levels after eating. Foods with a high GI (i.e., 70 or more) are those that are rapidly digested and absorbed and result in marked fluctuations in blood sugar levels. High GI foods include bread, rice, cereal and baked goods. Low GI (i.e., 55 or less) foods are slowly digested and absorbed and result in gradual rises in blood sugar and insulin levels. Low GI foods include fruits, vegetables, whole grains and legumes. Low GI diets have been shown to improve both glucose and lipid levels in people with Type 1 and Type 2 diabetes. They have benefits for weight control because they help control appetite and delay hunger. Low GI diets also reduce insulin levels and insulin resistance.

In order to achieve weight loss or to reduce the broad symptoms of metabolic syndrome or diabetes, the metabolic pathways of carbohydrate metabolism must be affected. Specifically, pathways can be affected by (1) inhibiting carbohydrate breakdown (2) inhibiting glucose absorption and transport from the gut to the bloodstream, (3) enhancing glucose absorption and transport into muscle tissue (4) inhibiting or reducing carbohydrates being stored as fat, (5) inhibiting gluconeogenesis, and (6) enhancing glucose liberation from fats. For the treatment of diabetes, it is necessary to affect pathways (2), (3), (5) and (6). To obtain weight loss and/or weight control, it is necessary to affect pathways (2) to (6). Although it is not necessary to affect pathway (1) for the treatment of diabetes or to obtain weight loss, it is beneficial to do so.

There are several naturally occurring compounds that have an effect on at least one of the metabolic pathways to some degree. Bioflavonoids, and in particular, flavanones and flavones are useful. Flavanones have the structure (I) shown below and flavones have the similar structure (II) shown below:

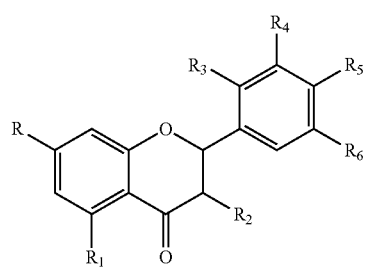

Flavanones (I)

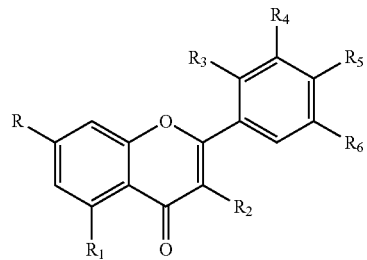

Flavones (II)

wherein R, $R_1$, $R_2$, $R_3$, $R_4$, $R_5$ and $R_6$ are each independently hydrogen, a hydroxy group, an alkoxy group, a rutinosyl group, a rhamnosyl group, a substituted alkoxy group or a substituted acyloxy group wherein the substituent is chosen from hydroxyl, alkoxy, aryloxy, phenyl, halogen, and amido group. Several examples of the bioflavonoids of formula (I) and (II) are shown below in Table 1.

TABLE 1

| | R | $R_1$ | $R_2$ | $R_3$ | $R_4$ | $R_5$ | $R_6$ |
|---|---|---|---|---|---|---|---|
| FLAVONE | | | | | | | |
| Flavone | H | H | H | H | H | H | H |
| Chrysin | OH | OH | H | H | H | H | H |
| Apigenin | OH | OH | H | H | H | OH | H |
| Luteolin | OH | OH | H | H | H | OH | H |
| Diosmin | —O-rutinose | OH | H | H | OH | OCH$_3$ | H |
| Fisetin | OH | H | OH | H | OH | OH | H |
| Kaempferol | OH | OH | OH | H | H | OH | H |
| Morin | OH | OH | OH | OH | H | OH | H |
| Quercetin | OH | OH | OH | H | OH | OH | H |
| Myricetin | OH | OH | OH | H | OH | OH | OH |
| Rutin | OH | OH | —O-rutinose | H | OH | OH | H |
| Rhoifolin | R—G—$^a$ | OH | H | H | H | OH | H |
| FLAVANONE | | | | | | | |
| Galangin | OH | OH | OH | H | H | H | H |
| Hesperetin | OH | OH | H | H | OH | OCH$_3$ | H |
| Eriodictyol | OH | OH | H | H | OH | OH | H |
| Naringenin | OH | OH | H | H | H | OH | H |
| Naringin | R—G—$^a$ | OH | H | H | H | OH | H |
| Neohesperidin | R—G—$^b$ | OH | H | H | OH | OCH$_3$ | H |
| Hesperidin | R—G—$^b$ | OH | H | H | OH | OCH$_3$ | H |
| Narirutin | R—G—$^b$ | OH | H | H | H | OH | H |
| Prunin | Glucose- | OH | H | H | H | OH | H |

$^a$rhamnose-glucose, L-rhamnose is linked α 1→2 to D-glucose
$^b$rhamnose-glucose, L-rhamnose is linked α 1→6 to D-glucose None of the bioflavonoids affect all of the metabolic pathways, and those that affect a particular pathway are not equally effective. In addition, many of the bioflavonoids are easily oxidized and are not heat stable. As a food additive, many of the bioflavonoids are not suitable because they impart a bitter or adverse taste to the food at therapeutically effective amounts.

It has been discovered that the combination of quercetin, myricetin and chlorogenic acid has a superior therapeutic effect on carbohydrate metabolism, and is particularly useful in the treatment of obesity and diabetes, and to achieve weight loss and/or weight control. This combination of naturally occurring compounds cannot be found in nature from any single source. In one embodiment, the composition comprises a ratio of chlorogenic acid to quercetin to myricetin of about 1:(2-4):(2-4), or about 1:(2-3):(2-3), or about 1:3:3 by weight.

A composition comprising quercetin, myricetin and chlorogenic acid may be administered as a dietary supplement or as an additive to a foodstuff. The composition may be incorporated into a foodstuff that is later cooked or baked. The components of the composition are structurally stable to remain un-oxidized and are heat stable at temperatures required for baking or cooking. When added to a carbohydrate-containing foodstuff in an effective amount, the composition enables a diabetic (or non-diabetic) person to consume the foodstuff without experiencing the same glycemic response as that of the foodstuff without the composition added thereto. Thus the foodstuff may be converted from a high GI (i.e., 70 or more) food to a medium GI (i.e., 56-69) or low GI (i.e., 55 or less) food, making the foodstuff safer for diabetics to consume.

Quercetin

Quercetin is a bioflavonoid found in many plants, including onions, celery, grapes, lemons, grapefruit and cranberries, to name a few. The primary metabolic pathway inhibition mechanism of quercetin is to cause GLUT2 transport inhibition, which slows glucose absorption from the gut. The secondary mechanism of quercetin is to cause glycogenolysis by lipid hydrolysis, which releases glucose from adipose tissue. The tertiary mechanism of quercetin is to inhibit fatty acid synthase (lipogenesis), which reduces the body's ability to store glucose as fat.

Myricetin

Myricetin is a bioflavonoid found in most berries, including cherry, cranberry and bilberry, and other plants, including parsley and rutabagas. The primary metabolic pathway inhibition mechanism of myricetin is to inhibit glucosidase, which inhibits or reduces the breakdown of starches, resulting in less available carbohydrates. The secondary mechanism of myricetin is to stimulate GLUT4 pathway, which enhances the uptake of glucose into muscle and skeletal tissue, resulting in less available glucose for storage as fat. The tertiary mechanism of quercetin is to inhibit the absorption of fructose.

There are several methods by which the quercetin and/or myricetin may be harvested from their original botanical sources. In one method, for example, extraction from botanical sources begins with a suitable seed material such as grape seeds or tomato seeds, pine bark or citrus rinds. The source material is macerated and flushed with water to separate the water soluble bioflavonoids from the bulkier pectins and fibers of the source material. This pulp wash is then treated with appropriate acids and bases as known in the art to cause precipitation. The precipitate is then washed again, dried and then concentrated to yield a fairly pure bioflavonoid composition. This composition may be further clarified to yield fractions containing the desired bioflavonoid product.

In another method, reverse osmosis may be used to remove the target bioflavonoid by filtering it out of juice streams from beverage manufacturing processes. The process of manufacturing fruit juices such as citrus, liberates the bioflavonoids from the rind and suspends them in the juice product. It is often desirable to remove these water soluble bioflavonoids because of their tendency to produce bitter or off flavors in the juice product. For example, during the manufacture of grapefruit juice, the primary grapefruit bioflavonoid naringin is released into the juice stream. Because naringin has a very distinct bitter taste, it is necessary to remove it from the product stream via the use of resin coated reverse osmosis devices to restore the proper flavor profile of the grapefruit juice. The resultant bioflavonoid is finally collected and dried to yield a fairly pure product.

The flavonoids may also be manufactured by synthetic methods. Such methods may include an Allan-Robinson Reaction which is a chemical reaction of o-hydroxylaryl ketones with aromatic anhydrides to form flavanones. Another example is Auwers Synthesis, which is a procedure that requires an acid catalyzed aldol condensation between benzaldehyde and a 3-oxypentanon to an o-hydroxychalcone. Further bromination of the alkene group gives a dibromoadduct that rearranges to a flavanol by reaction with potassium hydroxide. A further example is a Baker-Venkataraman Rearrangement, which involves the reaction of 2-acetoxyacetophenones with base to form 1,3-diketones. The rearrangement reaction proceeds via enolate formation followed by an acyl transper to form flavanones. An Algar-Flynn-Oyamada Reaction may also be used. In this reaction, a chalcone undergoes an oxidative cyclization to form a flavanol.

Chlorogenic Acid

Chlorogenic acid is one or more of a family of esters that form between certain cis or trans cinnamic acids and quinic acid. Chlorogenic acid may be subdivided by the identity, number and position of the acyl residues on the quinic acid. Examples of chlorogenic acid and functional analogs thereof may be represented by the formula (III):

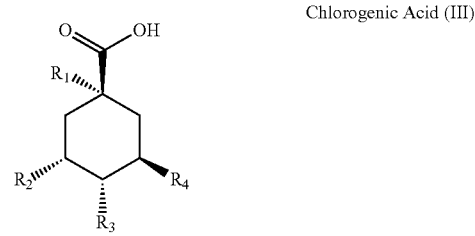

Chlorogenic Acid (III)

wherein at least one of the functional groups $R_1$-$R_4$ independently represents a cinnamic acid functional group represented by formulas (IV) to (VII).

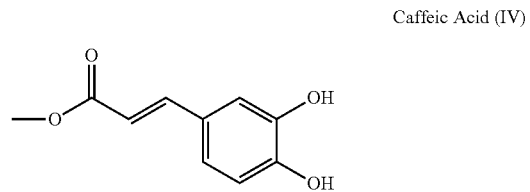

Caffeic Acid (IV)

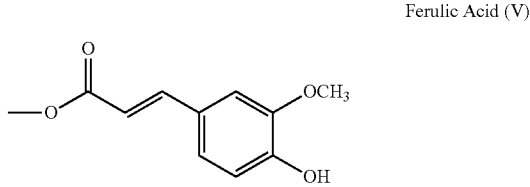

Ferulic Acid (V)

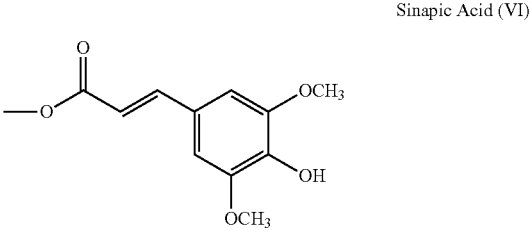

Sinapic Acid (VI)

p-Coumaric Acid (VII)

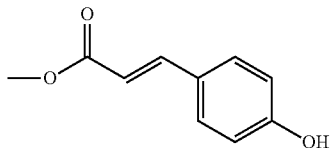

Cinnamic acids and their derivatives include a series of 3-phenyl-propenoic acids that differ in the chemical groups substituted on the aromatic ring. The most common of the cinnamic acids are caffeic acid, ferulic acid, sinapic acid and p-coumaric acid. Chlorogenic acid and several of its preferred functional analogs have the following chemical structures:

TABLE 2

| Compound | $R_1$ | $R_2$ | $R_3$ | $R_4$ |
|---|---|---|---|---|
| quinic acid | OH | OH | OH | OH |
| 1-O-caffeoyl quinic acid | (IV) | OH | OH | OH |
| 5-O-caffeoylquinic acid | OH | OH | OH | (IV) |
| 4-O-caffeoylquinic acid | OH | OH | (IV) | OH |
| 3-O-caffeoylquinic acid | OH | (IV) | OH | OH |
| 1,3-O-dicaffeoylquinic acid | (IV) | (IV) | OH | OH |
| 1,5-O-dicaffeoylquinic acid | (IV) | OH | OH | (IV) |
| 3,4-O-dicaffeoylquinic acid | OH | (IV) | OH | OH |
| 3,5-O-dicaffeoylquinic acid | OH | (IV) | OH | (IV) |
| 4,5-O-dicaffeoylquinic acid | OH | OH | (IV) | (IV) |
| 1,2,3,4,-O-tetracaffeoylquinic acid | (IV) | (IV) | (IV) | (IV) |
| 3-O-feruloyl quinic acid | OH | (V) | OH | OH |
| 4-O-feruloyl quinic acid | OH | OH | (V) | OH |
| 5-O-feruloyl quinic acid | OH | OH | OH | (V) |
| 3-O-p-coumaroyl quinic acid | OH | (VII) | OH | OH |
| 4-O-p-coumaroyl quinic acid | OH | OH | (VII) | OH |
| 5-O-p-coumaroyl quinic acid | OH | OH | OH | (VII) |

The chlorogenic compound used is preferably derived from a natural occurring source, e.g., as an extract of one or more plants. For example, it may be extracted from green coffee beans, green cacao beans, cinnamon, hawthorn, green tea, pome fruits such as apples and pears, stone fruits such as cherries and plums, berry fruits, citrus fruits, brassica vegetables such as kale, cabbage and brussel sprouts, solanaceae such as potato tubers, tomatoes and eggplant. It may also be derived from cereal grains such as oats, barley, rye, rice, corn and wheat. The amount and type of chlorogenic acid obtained depends upon the particular source.

The primary metabolic pathway inhibition mechanism of chlorogenic acid is the inhibition of alpha-amylase, which inhibits the breakdown of complex carbohydrates into transportable form. The effect reduces the amount of carbohydrates that can be absorbed. The secondary mechanism is the inhibition of Glucose 6 phosphate, which reduces hepatic gluconeogenesis. It reduces the liver's ability to make glucose.

In one embodiment of the invention, there is provided a composition comprising about 50 to about 500 mg quercetin; about 50 to about 500 mg myricetin; and about 25 to about 150 mg chlorogenic acid. In another embodiment, the composition comprises about 100 to about 200 mg quercetin; about 100 to about 200 mg quercetin; and about 30 to about 75 mg chlorogenic acid.

The composition may be administered in the form of a dietary supplement, a food or beverage additive or as a pharmaceutical composition. In addition to quercetin, myricetin and chlorogenic acid, the composition may include one or more additives.

Wetting agents, emulsifiers and lubricants, such as sodium lauryl sulfate and magnesium stearate, as well as coloring agents, release agents, coating agents, sweetening, flavoring agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like: (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, each containing a predetermined amount of a compound of the present invention as an active ingredient.

In solid dosage forms of the invention for oral administration, the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

In one embodiment of the invention, the composition is administered in the form of a beverage or foodstuff. For example, the composition can be added to baked goods such as cookies, brownies, crackers, breakfast bar, energy bar, cereal and cake. The composition may be added to a fruit juice, a carbonated beverage, an energy drink, coffee or tea. The quercetin, myricetin and chlorogenic acid are heat stable and will not oxidize during storage.

The individual components of the composition, namely quercetin, myricetin and chlorogenic acid, do not have any direct chemical or physical reaction with the carbohydrates of the food consumed. Rather, the effect on carbohydrate metabolism is due to a direct chemical reaction of the components with the enzymes involved in carbohydrate metabolism. Therefore, the effects are determined by the chemical reaction rate, which in turn is determined by the concentration of the flavonoid components and the components of the enzymatic systems, such as GLUT2 and GLUT4.

In one embodiment, the effective concentration for a composition consisting of a 1:3:3 mixture by weight of chlorogenic acid, myricetin and quercetin ranges from about 200 mg to about 500 mg of the composition consumed along with food. In one embodiment, a single dose per day, taken at the beginning of the day, is about 750 mg. In another embodiment, the composition is administered as a dose three times a day in an amount of about 250 mg per dose. The total amount of the composition administered daily, in one embodiment is at least 250 mg, or at least 500 mg, or at least 750 mg or at least 900 mg.

Because there can be no control over the amount of food an individual subject consumes, in order to deliver about 250 mg of the composition per typical serving, the concentration of composition varies according to the type of food and the typical serving size of that food. For example, as illustrated below, the concentration of the composition varies as the food varies:

| Food Item | Typical Serving Size | Composition | Concentration |
| --- | --- | --- | --- |
| Cola | 336 ml | 250 mg | 0.75 mg/ml |
| Juice | 168 ml | 250 mg | 0.67 mg/ml |
| Cookie | 40 g | 250 mg | 6.25 mg/g |
| Brownie | 75 g | 250 mg | 3.33 mg/g |

When the foodstuff comprises a beverage, the composition may be added to the beverage in an amount of about 0.5 to about 1.5 mg per ml of beverage. When the foodstuff comprises baked goods, the composition may be added to the baked goods in an amount of about 2.5 mg to about 10 mg per gram of baked goods.

Embodiments of inventive compositions and methods are illustrated in the following examples. These examples are provided for illustrative purposes and are not considered limitations on the scope of inventive compositions and methods.

EXAMPLES

Example 1

A gelatin capsule containing 50 mg chlorogenic acid, 200 mg myricetin and 200 mg quercetin is administered orally to a subject 3 times per day, taken with food.

Example 2

A tablet containing sodium citrate, 100 mg carboxymethylcellulose, 100 mg chlorogenic acid, 300 mg myricetin and 300 mg quercetin is administered orally once a day upon rising.

Example 3

Bread is manufactured to include 50 mg chlorogenic acid, 150 mg myricetin and 50 mg quercetin per 15 grams of total carbohydrates in the bread.

Example 4

Gingerbread cookies are manufactured to include 75 mg chlorogenic acid, 100 mg myricetin and 100 mg quercetin per approximately 30 g serving of cookie.

Example 5

A 100 g sports power bar is manufactured to include 75 mg chlorogenic acid, 300 mg myricetin and 300 mg quercetin.

Example 6

A powder containing 50 mg chlorogenic acid, 100 mg myricetin and 100 mg quercetin is sprinkled onto foods such as, for example scrambled eggs after cooking but prior to consumption.

Example 7

A composition containing a blend of 14% by weight chlorogenic acid, 52% by weight myricetin and 34% by weight quercetin is blended into a natural juice product, such as grapefruit juice, such that there is 1 mg of the composition per 1 g of juice.

Example 8

A 1:3:3 ratio by weight of chlorogenic acid, myricetin and quercetin is suspended in an elixir that is micro-encapsulated via air-suspension coating. The micro-encapsulated material is added to a brownie mix in an amount of 2 mg of microencapsulated material per 1 g of brownie. The brownie mix is sold as a dry mix for home or commercial baking, or the brownie is baked and sold as baked goods.

Example 9

A 1:3:3 ratio by weight of chlorogenic acid, myricetin and quercetin is dissolved in a sucrose sugar solution. It is crystallized to form a table sugar that has the flavonoids incorporated into its structure. The sugar product is used as a flavoring in other foodstuffs as in standard sucrose sugar, from coffee to baked goods.

While the invention has been explained in relation to various embodiments, it is to be understood that various modifications thereof will be apparent to those skilled in the art upon reading the specification. The features of the various embodiments of the articles described herein may be combined within an article. Therefore, it is to be understood that the invention described herein is intended to cover such modifications as fall within the scope of the appended claims.

What is claimed:

1. A method of treating diabetes or obesity in a subject, the method comprising administering to the subject a composition consisting of therapeutically effective amounts of quercetin, myricetin and chlorogenic acid.

2. The method of claim 1 wherein the composition comprises about 50 mg to about 500 mg quercetin; about 50 to about 500 mg myricetin and about 25 to about 150 mg chlorogenic acid.

3. The method of claim 1 wherein the composition comprises about 100 mg to about 200 mg quercetin; about 100 to about 200 mg myricetin and about 30 to about 75 mg chlorogenic acid.

4. The method of claim 1 wherein the ratio of chlorogenic acid to quercetin to myricetin is about 1:3:3.

5. The method of claim 1 wherein the subject is administered at least 750 mg of the composition daily.

6. A method of lowering the glycemic index of a carbohydrate-containing foodstuff comprising adding to the foodstuff an effective amount of a composition consisting of quercetin, myricetin and chlorogenic acid, wherein said composition is added to reduce the glycemic index of the carbohydrate-containing foodstuff.

7. The method of claim 6 wherein the foodstuff is a beverage and the composition is added to the beverage in an amount of about 0.5 to about 1.5 mg per ml of beverage.

8. The method of claim 6 wherein the foodstuff is baked goods and the composition is added to the baked goods in an amount of about 2.5 mg to about 10 mg per gram of baked goods.

9. The method of claim 6 wherein the composition comprises a ratio of chlorogenic acid to quercetin to myricetin of about 1:3:3 by weight.

* * * * *